United States Patent [19]

Paulus et al.

[11] 4,187,855
[45] Feb. 12, 1980

[54] GARMENT FOR USE AFTER BREAST SURGERY

[76] Inventors: Cornelia A. Paulus; Nancy E. Paulus, both of 6719 Briargate, Downers Grove, Ill. 60515

[21] Appl. No.: 808,973

[22] Filed: Jun. 22, 1977

[51] Int. Cl.² .............................................. A41C 3/00
[52] U.S. Cl. ........................................ 128/427; 2/104
[58] Field of Search ............ 128/425, 427, 430, 431, 128/454, 460, 461, 478, 481; 2/67, 104

[56] References Cited

U.S. PATENT DOCUMENTS

| | | | |
|---|---|---|---|
| 2,491,360 | 12/1949 | Brown | 2/67 |
| 2,550,327 | 4/1951 | Christensen | 2/67 |
| 2,614,257 | 10/1952 | Kramer et al. | 128/454 |
| 2,918,920 | 12/1959 | Lutsky | 128/431 |
| 3,255,754 | 6/1966 | Brumberger | 2/67 |
| 3,447,538 | 6/1969 | Keown | 128/478 |
| 3,490,459 | 1/1970 | Story | 128/454 |
| 3,498,297 | 3/1970 | Lord | 128/478 |
| 3,628,539 | 12/1971 | Fredricks | 128/427 |
| 3,701,168 | 10/1972 | Balow | 128/481 |
| 3,826,266 | 7/1974 | Alpert | 128/481 |

*Primary Examiner*—Doris L. Troutman
*Attorney, Agent, or Firm*—James J. Conlon & Associates

[57] ABSTRACT

A prosthesis, or brassiere-type garment, to be worn after breast surgery, which includes enlarged arm openings and an elongated bodice portion to fit beyond the wearer's waist and assist in holding the garment in place. A breast substitute is provided in the form of a swimsuit insert, a conventional padded bra, or other device which may be filled with a suitable padding material and attached to the garment.

8 Claims, 9 Drawing Figures

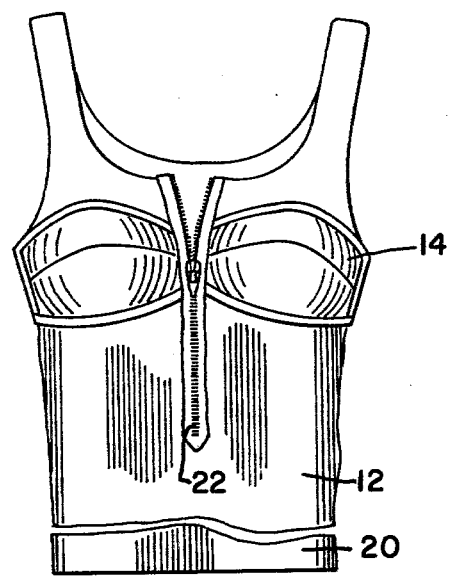
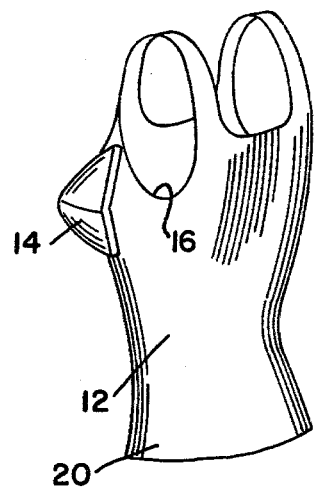
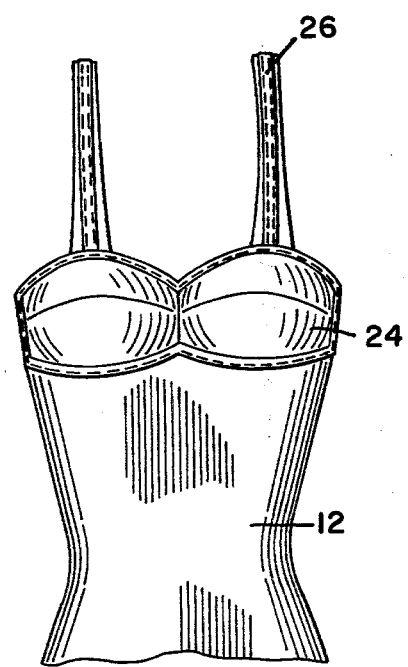
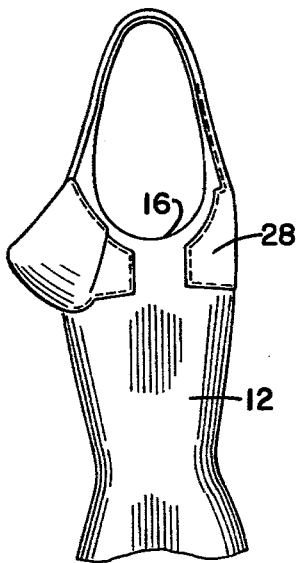
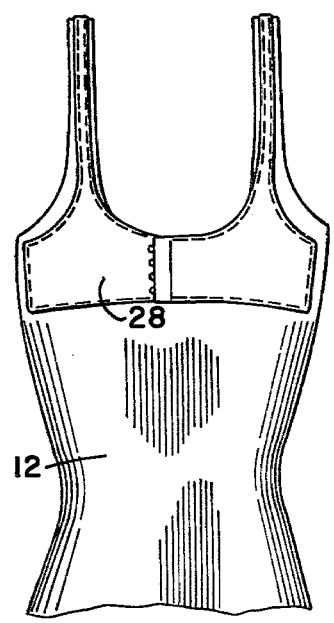

4,187,855

GARMENT FOR USE AFTER BREAST SURGERY

BACKGROUND OF THE INVENTION (1) Field of the Invention

This invention pertains to an undergarment worn by women who have undergone single as well as bilaterial or radical mastectomies.

(2) Description of the Prior Art

Following breast surgery, a woman is inflicted with not only tremendous physical discomfort but also the emotional stress of feeling she has an unnatural appearance. Upon leaving the hospital following surgery it is desirable to provide the surgical patient with a natural appearance through the use of a brassiere-type garment that is natural appearing, yet comfortable. Prior art devices such as the Balow, U.S. Pat. No. 3,701,168 (1972), and Keown, U.S. Pat. No. 3,447,538 (1969), have attempted to provide natural appearing, comfortable brassiere-type garments. However, these prior art devices have not met with widespread acceptance for a number of reasons. Primarily, the devices have not been accepted because they are uncomfortable if worn immediately after surgery because they are tightly attached where the surgical incisions have been made and which remain tender for up to three months after the surgery. Consequently, these prior art devices which must be tightly attached to the upper chest portion are irritating to the recent surgery patient.

Furthermore, the prior art devices have not been completely acceptable because they cannot be reliably held in place when the wearer engages in normal, everyday activity. Normal brassieres are held in place during the wearer's activity because the cup portions are filled with a breast which acts to hold the brassiere in place. With a prosthesis there is no human portion that fits within the brassier to hold it in place. Consequently, a woman recovering from breast surgery needs a comfortable device that will hold the breast substitute in place during everyday activity and to prevent the embarrassment of constantly having to align and adjust the brassiere.

SUMMARY OF THE INVENTION

This invention pertains to a device to be worn by women who have undergone breast surgery and which provides a natural appearing substitute that is comfortable, easily held in place on the wearer, and can be worn immediately after surgery.

The garment is formed by providing a conventional man's sleeveless undershirt that has the desirable swiss-knit woven construction. A swimsuit bra insert is attached in the proper place and partially sewn into position and thereafter filled with a suitable material to maintain the desirable bust form and position.

When placed on the wearer the swiss-knit construction of the undershirt allows the garment to cling snugly to a larger portion of the wearer's body. The elongated structure of the undershirt permits the lower portion of the bodice to extend down below the wearer's waistband to provide even more contact with the body to hold the garment in place. Thus, the garment hugs the wearer's body and evenly distributes holding forces about the wearer's upper trunk and waist. By evenly gripping the wearer no tight and uncomfortable, localized forces are applied to the wearer which could cause pain and irritation in the incision area.

Modifications of the garment may occur by providing a zipper in the front portion to permit the garment to be more easily placed upon the wearer. Another modification involves alteration of the front portion of the undershirt and the straps that extend over the wearer's shoulder to resemble a brassiere and thereby allow the garment to be worn with evening gowns, low-cut dresses, sheer blouses and the like.

These and other objects of the invention will become apparent to those persons having ordinary skill in the art with reference to the following description, drawings and claims.

BRIEF DESCRIPTION OF THE DRAWINGS

FIG. 5 is a side, rear pictorial illustration showing the garment;

FIG. 6 is a front view of a modification of the garment utilizing a zipper front;

FIG. 7 is a front view of yet another modification of the garment with the upper portion having a bra strap appearance;

FIG. 8 is a side elevational view of the garment illustrated in FIG. 7; and

FIG. 9 is a rear view of the garment illustrated in FIG. 7.

DETAILED DESCRIPTION

Figure 1:
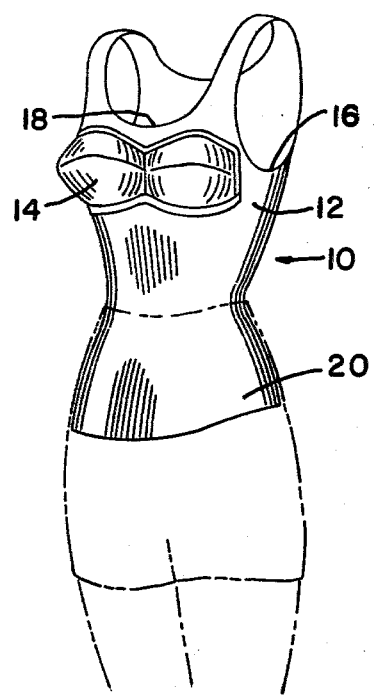
FIG. 1 is a pictorial illustration of the garment with the wearer's low body portion shown in phantom.

Referring now to the drawings and in particular FIG. 1 the garment is shown pictorially and referred to by the numeral 10. The garment may be constructed from a man's athletic undershirt 12 that has a swiss-knit construction. It is recommended that the athletic, sleeveless undershirt be of a 65% Kodell polyester and 35% cotton combination. The inclusion of the cotton in the blend for the garment provides a small percentage of shrinkage which helps to hold the garment in place on the wearer after washing.

Figure 2:
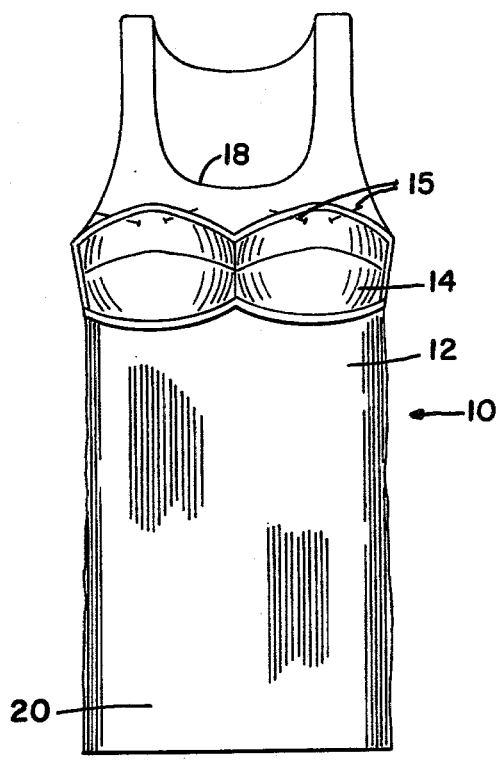
FIG. 2 is a front elevational view of the garment showing a swimsuit insert pinned in place prior to being sewn on the undershirt.
Figure 3:
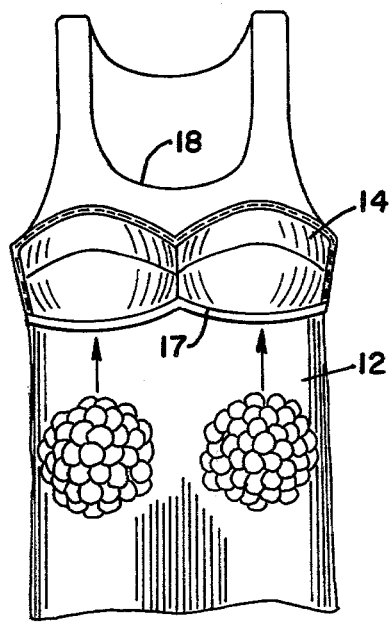
FIG. 3 shows a partially attached position of the bra insert before a filler material is inserted therein to provide the desirable breast contour.

As shown in the illustrations and in particular FIG. 1, a swimsuit bra insert 14 is attached to the upper front portion of the undershirt 12. The swimsuit insert 14 may initially be held in place by straight pins as shown in FIG. 2 for proper alignment and positioning. The swimsuit bra insert is a kind generally found in most department stores such as that manufactured by the Quick-Sew Corporation which is sold by Minnesota Fabrics under catalogue number WB461-25, 26, 27, 28 corresponding with cup sizes A, B, C and D, respectively. The soft side of the bra insert is positioned on the outside and the rougher surface, if any, is on the inside that is filled. As shown in FIG. 3, the swimsuit bra insert 14 is sewn in position along the top and side hems with the bottom hem left open for insertion of a filler material. It is suggested that a polyester fiberfill material be used to provide the padding insert which helps hold the bust form of the swimsuit bra insert 14. After the filler material is inserted, the seams 17 are sewn closed.

It is noticed in FIGS. 1 and 5 that the sleeveless, athletic undershirt used with this garment provides a number of significant features. Because a radical mastectomy operation involves extensive scarring and suturing in the frontal chest cavity and in the armpit area, it is necessary to provide an undergarment having enlarged arm openings 16. Thus, by eliminating tight fabric in the underarm area much irritation is eliminated with this garment.

Figure 4:
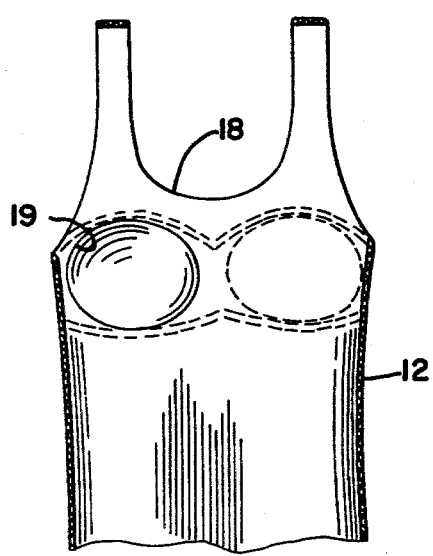
FIG. 4 is a sectional view from the rear of the garment.

If an unilaterial mastectomy has occurred, one breast removed, a part of the shirt may be removed to provide an opening 19 (FIG. 4) for the natural breast.

To overcome the problem of the breast shape becoming misaligned or moving vertically when the wearer engages in activities the undershirt garment 12 has an elongated bodice 20. Bodice 20 extends downwardly beyond the wearer's waistline, to firmly grip the body from below the waist to the upper trunk area. The swiss-knit construction allows the undershirt 21 to expand laterally and conform to the contour of the wearer's body. Thus, when being worn, the undershirt fits snugly, but not tightly, to a large portion of the wearer's body in a uniform gripping fashion as to hold the brassiere portion securely in place.

Modification of the configuration shown in FIG. 1 is shown in FIG. 6 wherein a short zipper is added between the cup portions of the bra insert 14. By using a zipper the garment may be more easily attached about the upper chest cavity to prevent irritation immediately after surgery and yet provide a garment that is securely held in place after it is properly positioned on the post-surgical patient.

Another embodiment is shown in FIGS. 7, 8 and 9 wherein the undershirt 12 is modified to provide an appearance of a conventional brassiere strap, shoulder strap and rear strap appearance. As shown in FIG. 7, the front portion of the undershirt 12 is scooped and conforms with the contour of the upper portion of the bra insert or bra front 24. The undershirt straps 26 may be narrowed somewhat to conform to the thickness of the bra strap and providing natural appearance. As shown in FIG. 8, the side expandable portion of the bra strap has been removed to allow expansion and contraction of the garment to depend solely upon the movement of the undershirt.

FIG. 9 shows that the back portion of the undershirt has also been scooped to conform to the upper contour of the bra back 28 and thereby provides a natural appearance and permits the wearer to use conventional garments without showing that a prosthetic device is being worn.

In attaching a conventional bra to produce the garment shown in FIGS. 6, 7, 8 and 9, the front portion of the bra is pinned in place until a proper position is obtained and the top and sides are sewn in position. Thereafter, the fiberfill material is inserted followed by sewing of the bottom portion of the bra front to the shirt.

A seamless bra is recommended to be adapted for this construction and it has been found that a Montgomery Ward's Style 3886 or a J.C. Penney's Style 2250 that are padded, and seamless are suitable for this use. It has been found that padding provides a more rigid construction that continues to provide the requisite form which keeps shape after several washings.

Thus, it has been shown that the garment provided by this invention allows a post-surgical mastectomy patient to appear natural and also be very comfortable in wearing a breast substitute. The garment provided herein clings to the body in a comfortable fashion and is held in place by the unique construction disclosed herein that utilizes a form fitting bodice portion of a garment that clings to the wearer's body in an unobtrusive, almost invisible manner.

The foregoing description and drawings merely explain and illustrate the invention and the invention is not limited thereto, except insofar as the appended claims are so limited, as those who are skilled in the art have the disclosure before them will be able to make modifications and variations therein without departing from the scope of the invention.

What is claimed is:

1. A garment to be worn after breast surgery having brassier-type mammary prosthesis to emulate a natural breast appearance of a wearer, the improvement comprising:
    a body hugging, seamless shirt having a front and a back and a smooth interior adapted to fit snugly and comfortably about a person's body;
    said shirt having expandable fabric means adapted to cling to and firmly hold the shirt in place on the wearer;
    said shirt having a pair of enlarged arm openings and shoulder strap means associated with each arm opening;
    an elongated bodice with an extension with an open body for extending beyond and around the wearer's waist to assist in holding the shirt in place; prosthesis type bra means with means attached to the top front outside of said shirt leaving the bottom of said bra unattached without obstructing the smooth interior of the seamless outside shirt and said bra means having filler mean and then attaching the bottom of the bra means to said shirt providing a two-breast natural appearance garment to the wearer which will not ride up and stays in place on the wearer and cannot be easily observed through or be otherwise visible under outer garments.

2. The shirt of claim 1 wherein said fabric means includes:
    a swiss knit construction providing rib means extending longitudinally along the height of the wearer to thereby allow the expandable fabric means to fit snugly about the wearer and to adapt to the contour of the wearer's body in a natural, comfortable fashion.

3. The invention according to claim 1 wherein said bra means includes:
    at least one hollow portion having a breast shape;
    filler means composed of a soft, resilient material within said hollow portion.

4. The shirt of claim 1 and:
    said shirt includes a pair of straps extending from the front of the shirt to the rear of the shirt over the wearer's shoulders.

5. The garment of claim 1 wherein said bra means includes:
    a front with cup portions;
    bra straps with means extending from said cup portions
    said bra means including a back with means aligned with the front;
    said back having means attached to said shirt and having end portions attached to the shirt adjacent each enlarged arm opening;
    said shirt providing an expandable connection between the back of the bra means and the bra means;

said back of the bra means including means connecting with the bra straps;

said shirt having a top front with means conforming to the outline of said bra front;

said shirt having a scooped back conforming with the back portion of the bra to thereby provide a natural bra appearance to the top portion of the garment.

6. The garment of claim 1 adaptable for use by a person having a unilateral mastectomy, the improvement comprising:

the front portion of the shirt having a cut-out providing access to said hollow portion within the bra insert to receive a natural breast.

7. The garment of claim 1 wherein the shirt includes:

zipper means;

said zipper movable between open and closed positions;

said zipper means having first means attached to the top front portion of the shirt and second, terminal means to allow the bra means to be positioned adjacent the wearer with the zipper in the open position and then securely held when the zipper is in the closed position.

8. A method of producing a brassier type mammary prosthesis garment comprising the steps of:

providing a body hugging, expandable shirt having a front portion;

positioning a bra means adjacent the top front portion of the shirt;

attaching the bra means temporarily to the shirt;

aligning the bra means;

attaching the sides and top portions of the bra means to the shirt;

filling the bra means with a padding material;

enclosing the bottom portion of the bra means.

* * * * *